(12) United States Patent
Kwon et al.

(10) Patent No.: US 11,720,791 B2
(45) Date of Patent: Aug. 8, 2023

(54) APPARATUS AND METHOD OF OPTIMIZING EXPERIMENTAL CONDITIONS USING NEURAL NETWORK

(71) Applicant: SAMSUNG ELECTRONICS CO., LTD., Suwon-si (KR)

(72) Inventors: Youngchun Kwon, Yongin-si (KR); Jinwoo Park, Suwon-si (KR); Dongseon Lee, Suwon-si (KR); Youngmin Nam, Gyeonggi-do (KR); Minsik Park, Hwaseong-si (KR); Jiho Yoo, Hwaseong-si (KR); Younsuk Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 411 days.

(21) Appl. No.: 16/887,062

(22) Filed: May 29, 2020

(65) Prior Publication Data

US 2021/0125060 A1    Apr. 29, 2021

(30) Foreign Application Priority Data

Oct. 29, 2019 (KR) .................. 10-2019-0135592

(51) Int. Cl.
*G06N 3/08* (2023.01)
*G06N 3/047* (2023.01)

(52) U.S. Cl.
CPC .............. *G06N 3/08* (2013.01); *G06N 3/047* (2023.01)

(58) Field of Classification Search
CPC ............ G06N 3/08; G06N 3/047; G06N 5/01; G06N 7/01; G06N 3/02; G06N 3/04; G16C 20/10
See application file for complete search history.

(56) References Cited

U.S. PATENT DOCUMENTS

| | | | |
|---|---|---|---|
| 2017/0007147 A1* | 1/2017 | Hasegawa | A61B 5/162 |
| 2018/0307805 A1* | 10/2018 | Dey | G16C 20/30 |
| 2020/0058298 A1 | 2/2020 | Ban et al. | |
| 2021/0049460 A1* | 2/2021 | Ahn | G06N 3/045 |
| 2021/0233620 A1* | 7/2021 | Cronin | G16C 20/10 |

FOREIGN PATENT DOCUMENTS

| | | |
|---|---|---|
| JP | 2003-39180 A | 2/2003 |
| KR | 10-2012-0085137 A | 7/2012 |
| KR | 10-2012-0085157 A | 7/2012 |
| KR | 10-2018-0042577 A | 4/2018 |

OTHER PUBLICATIONS

Gao, Hanyu et al., "Using Machine Learning To Predict Suitable Conditions for Organic Reactions", ACS Central Science, 2018, vol. 4, pp. 1465-1476. (12 pages total).

* cited by examiner

Primary Examiner — Edward Chin
(74) Attorney, Agent, or Firm — Sughrue Mion, PLLC (57) ABSTRACT

An apparatus for optimizing experimental conditions by using a neural network may calculate a prediction yield and accuracy of the prediction yield by using a neural network-based experimental prediction model. The apparatus may optimize the experimental conditions by determining an experiment priority of a respective experiment condition combination based on the prediction yield and the prediction accuracy and receiving a feedback of results of experiments performed according to the experiment priority.

17 Claims, 8 Drawing Sheets

|  | A | B | C | D | E |
|---|---|---|---|---|---|
| PREDICTION YIELD (%) | 91 | 63 | 72 | 84 | 86 |
| PREDICTION ACCURACY (%) | 94 | 87 | 91 | 93 | 96 |

EXPERIMENT PRIORITY: A E D C B

FIG. 4B

|  | A' | B' | C' | D' | E' |
|---|---|---|---|---|---|
| PREDICTION YIELD (%) | 24 | 33 | 37 | 31 | 25 |
| PREDICTION ACCURACY (%) | 28 | 91 | 84 | 79 | 38 |

⇒

EXPERIMENT PRIORITY

| A' | E' | D' | C' | B' |
|---|---|---|---|---|

APPARATUS AND METHOD OF OPTIMIZING EXPERIMENTAL CONDITIONS USING NEURAL NETWORK

CROSS-REFERENCE TO RELATED APPLICATION

This application claims priority from Korean Patent Application No. 10-2019-0135592, filed on Oct. 29, 2019, in the Korean Intellectual Property Office, the disclosure of which is incorporated by reference herein in its entirety.

BACKGROUND

1. Field

Example embodiments of the disclosure relate to apparatuses and methods of optimizing experimental conditions using neural networks.

2. Description of Related Art

Neural networks refer to a computer scientific computational architecture that models a biological brain. As neural network technology develops, input data is analyzed and valid information is extracted in various types of electronic systems by utilizing neural networks.

Recently, research for optimizing experimental conditions of synthetic experiments using neural network technology has been actively conducted. In particular, there is a need to develop a technique that may reduce the number of experiments and obtain a high yield by preferentially experimenting with optimal conditions of a synthetic experiment based on neural network technology.

SUMMARY

One or more example embodiments provide apparatuses and methods of optimizing experimental conditions by using a neural network, and a non-transitory computer-readable recording medium having a program recorded thereon for executing the methods on a computer. The technical problem to be solved by the example embodiments is not limited to the above technical problems, and further technical problems and technical solutions that solve the problems may be inferred from the following example embodiments.

Additional aspects will be set forth in part in the description which follows and, in part, will be apparent from the description, or may be learned by practice of the example embodiments of the disclosure.

According to an aspect of an example embodiment, there is provided a method of optimizing experimental conditions by using a neural network, the method including: receiving structural information of a reactant and structural information of a product; generating experimental condition combinations by combining one or more experimental conditions for producing the product; calculating a prediction yield of the product and a prediction accuracy of the prediction yield for each of the experimental condition combinations by using an experimental prediction model based on a neural network; determining an experiment priority of a respective experimental condition combination based on the prediction yield and the prediction accuracy; and updating the experimental prediction model based on a result of an experiment performed according to the experiment priority.

The determining may include selecting at least one experimental condition combination having the prediction accuracy greater than a predetermined reference accuracy, among the experimental condition combinations; and determining an experiment priority of the selected at least one experimental condition combination in an order of a high prediction yield.

The determining may include determining experiment priorities of the experimental condition combinations in an order of a low prediction accuracy when all of prediction yields of the experimental condition combinations are less than a predetermined reference yield.

The updating may include updating the experimental prediction model based on a measured yield of the product obtained with respect to an experimental condition combination having a high priority, in response to the measured yield being less than a predetermined target yield; and re-determining the experiment priority of an experimental condition combination having a low priority based on the updated experimental prediction model.

The updating the experimental prediction model may be repeated until the measured yield reaches a target yield.

The updating the experimental prediction model may be terminated when a number of a repetition of the updating reaches a preset reference number.

The determining may include generating experimental condition groups, each of the experimental condition combinations being included in any one of the experimental condition groups; and determining an experiment priority of a respective experimental condition combination included in each of the experimental condition groups.

The generating the experimental condition groups may include generating the experimental condition groups in a manner such that an experimental condition that most affects the prediction yield is not to be overlapped each other in the experimental condition groups.

The receiving may include receiving the structural information of the reactant and the structural information of the product in a form of an extended connectivity fingerprint (ECFP).

The one or more experimental conditions may include at least one of a catalyst condition, a base condition, a solvent condition, a reagent condition, a temperature condition, and a reaction time condition.

According to an aspect of an example embodiment, there is provided a neural network apparatus for optimizing experimental conditions, the neural network apparatus including: a user interface configured to receive structural information of a reactant and structural information of a product; a memory configured to store at least one program; and a processor configured to operate a neural network by executing the at least one program, wherein the processor is further configured to: generate experimental condition combinations by combining one or more experimental conditions for producing the product; calculate a prediction yield of the product and a prediction accuracy of the prediction yield with respect to each of the experimental condition combinations by using an experimental prediction model based on a neural network; determine an experiment priority of a respective experimental condition combination based on the prediction yield and the prediction accuracy; and update the experimental prediction model based on a result of an experiment performed according to the experiment priority.

The processor may be further configured to: select at least one experimental condition combination having the prediction accuracy greater than a predetermined reference accuracy, among the experimental condition combinations, and determine an experiment priority of the selected at least one experimental condition combinations in an order of a high prediction yield.

The processor may be further configured to determine experiment priorities of the experimental condition combinations in an order of a low prediction accuracy when all of prediction yields of the experimental condition combinations are less than a predetermined reference yield.

The processor may be further configured to: update the experimental prediction model based on a measured yield of the product with respect to an experimental condition combination having a high priority, in response to the measured yield being less than a predetermined target yield, and re-determine the experiment priority of an experimental condition combination having a low priority based on the updated experimental prediction model.

The processor may be further configured to repeat updating the experimental prediction model in response to the measured yield being less than the predetermined target yield.

The processor may be further configured to terminate the updating the experimental prediction model when a number of a repetition of the updating reaches a preset reference number.

The processor may be further configured to: generate experimental condition groups, each of the experimental condition combinations being included in any one of the experimental condition groups, and determine an experiment priority of a respective experimental condition combination included in each of the experimental condition groups.

The processor may be further configured to generate the experimental condition groups in a manner such that an experimental condition that most affects the prediction yield is not to be overlapped each other in the experimental condition groups.

According to an aspect of an example embodiment, there is provided a non-transitory computer-readable recording medium having a program recorded thereon, the program, when executed by a computer, causes the computer to execute the method described above.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Reference will now be made in detail to embodiments, examples of which are illustrated in the accompanying drawings, wherein like reference numerals refer to like elements throughout. In this regard, example embodiments may have different forms and should not be construed as being limited to the descriptions set forth herein. Accordingly, the example embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

The phrases "in some embodiments" or "in one embodiment" appearing in various places in the specification are not necessarily all referring to the same embodiment.

Some embodiments of the disclosure may be represented by functional block configurations and various processing operations. Some or all of the functional blocks may be implemented in various numbers of hardware and/or software configurations that perform particular functions. For example, the functional blocks of the disclosure may be implemented by one or more microprocessors or by circuit configurations for a given function. Also, for example, the functional blocks of the disclosure may be implemented in various programming or scripting languages. The functional blocks may be implemented in algorithms running on one or more processors. In addition, the disclosure may employ the related art for electronic configuration, signal processing, and/or data processing. Terms, such as "mechanism", "element", "means" and "configuration" may be used widely and are not limited to mechanical and physical configurations.

In addition, the connecting lines or connecting members between the components shown in the drawings are merely illustrative of functional connections and/or physical or circuit connections. In a practical device, the connections between the components may be represented by various functional connections, physical connections, or circuit connections that may be replaced or added.

In relation to the terminology used in the specification, a descriptor, which is data used in a neural network system, is an index value used to express a feature of a substance, and may be obtained by performing a relatively simple calculation process on a given substance. In one example embodiment, the descriptor may include a molecular structure fingerprint descriptor (for example, Morgan Fingerprint, Extended Connectivity Fingerprint (ECFP)) that indicates whether a particular partial structure is included or a quantitative structure-property relationships (QSPR) descriptor composed of values that may be readily calculated, such as the number of partial structure (for example, rings) contained in a molecular weight or molecular structure.

In addition, the structure may refer to a structure of an atom level of a material. The structure may be a structural formula based on a bond between atoms, or may be a simple text string (one-dimensional). A text string format representing a structure may include a simplified molecular-input line-entry system (SMILES) code, a miles arbitrary target specification (SMART) code, or an international chemical identifier (InChi) code.

Hereinafter, example embodiments of the disclosure will be described in detail with reference to the accompanying drawings.

Figure 1:
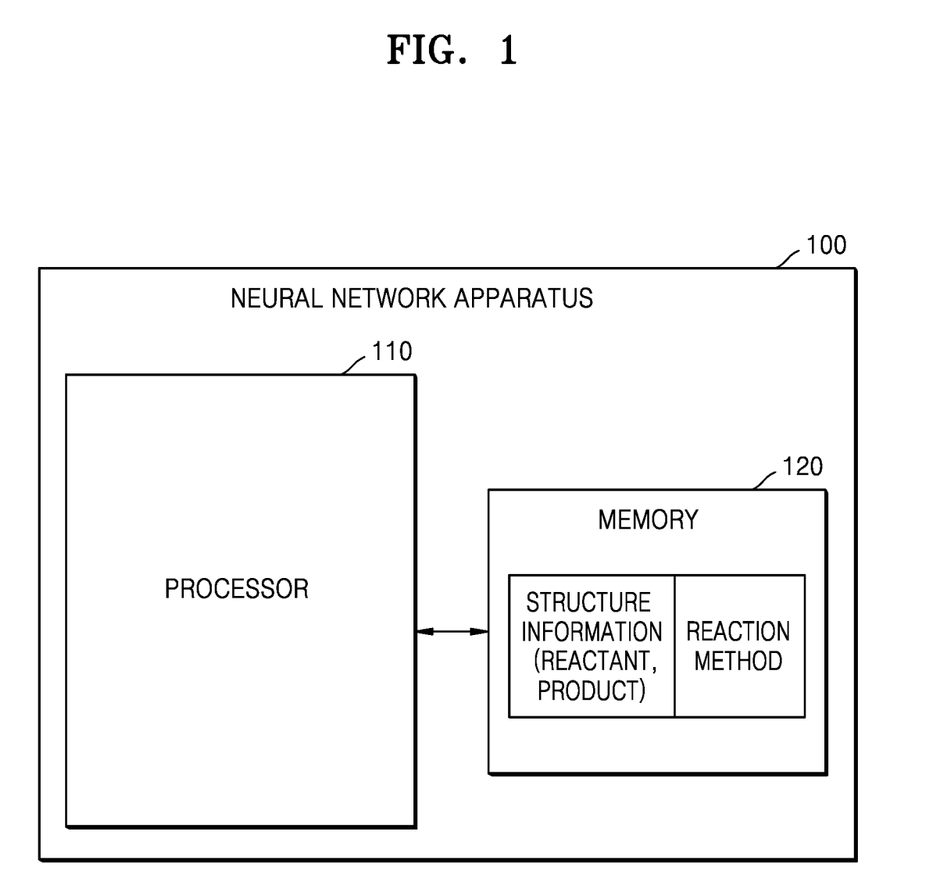
FIG. 1 is a block diagram illustrating a hardware configuration of a neural network apparatus according to an example embodiment.

FIG. 1 is a block diagram illustrating a hardware configuration of a neural network apparatus 100 according to an example embodiment.

The neural network apparatus 100 may be implemented with various kinds of devices, such as a personal computer (PC), a server, a mobile device, an embedded device, etc. and may correspond to, by way of examples, smartphones, tablet devices, augmented Reality (AR) devices, Internet of Things (IoT) devices, autonomous vehicles, robotics, and medical devices that perform voice recognition, image recognition, and image/or classification using neural networks, but is not limited thereto. Furthermore, the neural network apparatus 100 may correspond to an exclusive hardware (HW) accelerator mounted on the devices described above, and the neural network apparatus 100 may be an HW accelerator, such as a neural processing unit (NPU), a tensor processing unit (TPU), a neural engine, etc., which is an exclusive module for driving a neural network, but is not limited thereto.

Referring to FIG. 1, the neural network apparatus 100 includes a processor 110, a memory 120, and a user interface (not shown). In the neural network apparatus 100 shown in FIG. 1, only components related to the present embodiment are shown. Therefore, it will be apparent to those skilled in the art that the neural network apparatus 100 may further include other components in addition to the components shown in FIG. 1.

The processor 110 controls the overall functions for executing the neural network apparatus 100. For example, the processor 110 may control the neural network apparatus 100 as a whole by executing programs stored in the memory 120 in the neural network apparatus 100. The processor 110 may be implemented as a central processing unit (CPU), a graphics processing unit (GPU), an application processor (AP), etc., which are stored in the neural network apparatus 100, but is not limited thereto.

The memory 120 is hardware for storing various data processed in the neural network apparatus 100. For example, the memory 120 may store data processed and data to be processed in the neural network apparatus 100. Also, the memory 120 may store applications, drivers, etc. to be driven by the neural network apparatus 100. The memory 120 may include a random access memory (RAM), such as a dynamic random access memory (DRAM), a static random access memory (SRAM), a read-only memory (ROM), an electrically erasable programmable read-only memory (EEPROM), a CD-ROM, a Blue-ray or other optical disk storage, a hard disk drive (HDD), a solid state drive (SSD), or a flash memory.

A neural network-based experimental prediction model may be stored in the memory 120. The experimental prediction model may include a model generated by the processor 110 by machine learning based on a database, such as Reaxys or SciFinder. For example, the processor 110 may generate an experimental prediction model using a deep neural network (DNN), a recurrent neural network (RNN), a conditional Variational AutoEncoder (CVAE), etc., but is not limited thereto. The experimental prediction model may store structural information of reactants, structural information of products, and a predicted yield and a prediction accuracy according to a reaction method and experimental conditions. The processor 110 may modify the experimental prediction model by receiving a prediction yield and a prediction accuracy from the experimental prediction model or by receiving feedback from a user input.

The experimental prediction model may store structural information of reactants, structural information of products, and/or a reaction formula. The structural information may denote a structure feature value indicating whether a specific partial structure is included as an index value used to express the structure of a substance. For example, the structural feature value may be an extended connectivity fingerprint (ECFP).

The reaction model may refer to a chemical reaction method of producing a product by using reactants. For example, when product halide (R2-BY2) is produced by using reactant organoboron (R1-BY2), the reaction method may be a Suzuki-miyaura method. The reaction method may be provided in plurality according to the structural information of the reactants and the structural information of the products.

Also, the experimental prediction model may store at least one experimental condition corresponding to the reaction method.

Experimental conditions may denote various conditions that are set to perform an experiment to produce a product by using the reactants, and may be determined according to the reaction method. For example, the experimental conditions may include at least one of a catalyst, a base, a solvent, a reagent, a temperature, and a reaction time.

When the processor 110 receives structural information of a reactant and structural information of a product, which are not stored in the database, the processor 110 may output experimental condition combinations by which a high yield is expected based on the experimental prediction model. Also, the processor 110 may output a prediction yield and a prediction accuracy of a product corresponding to each of the experimental condition combinations.

The predicted yield may denote an expectation for yield of a product produced from the reactants and the predicted yield may be calculated by an experimental prediction model when reactants are tested under a certain reaction method and a certain experimental condition. The predicted yield may differ from a measured yield obtained by an actual experiment. The prediction accuracy may be an indicator of how close the prediction yield is to the measured yield.

A user interface (not shown) may denote an inputting method for receiving feedback of an experiment result. For example, the user interface may include a key pad, a dome switch, a touch pad (e.g., contact capacitive type, pressure resistive type, infrared beam type, surface acoustic wave type, integral strain gauge type, piezoelectric effect type, etc.), a jog wheel, a jog switch, etc., but is not limited thereto. The processor 110 may update the experimental prediction model by receiving feedback of the experiment result.

In the following description, methods of preferentially providing optimized experimental conditions by using the neural network apparatus 100 according to an example embodiment will be described in detail. Methods described below may be performed by the processor 110, the memory 120, and a user interface (not shown) of the neural network apparatus 100.

Figure 2:
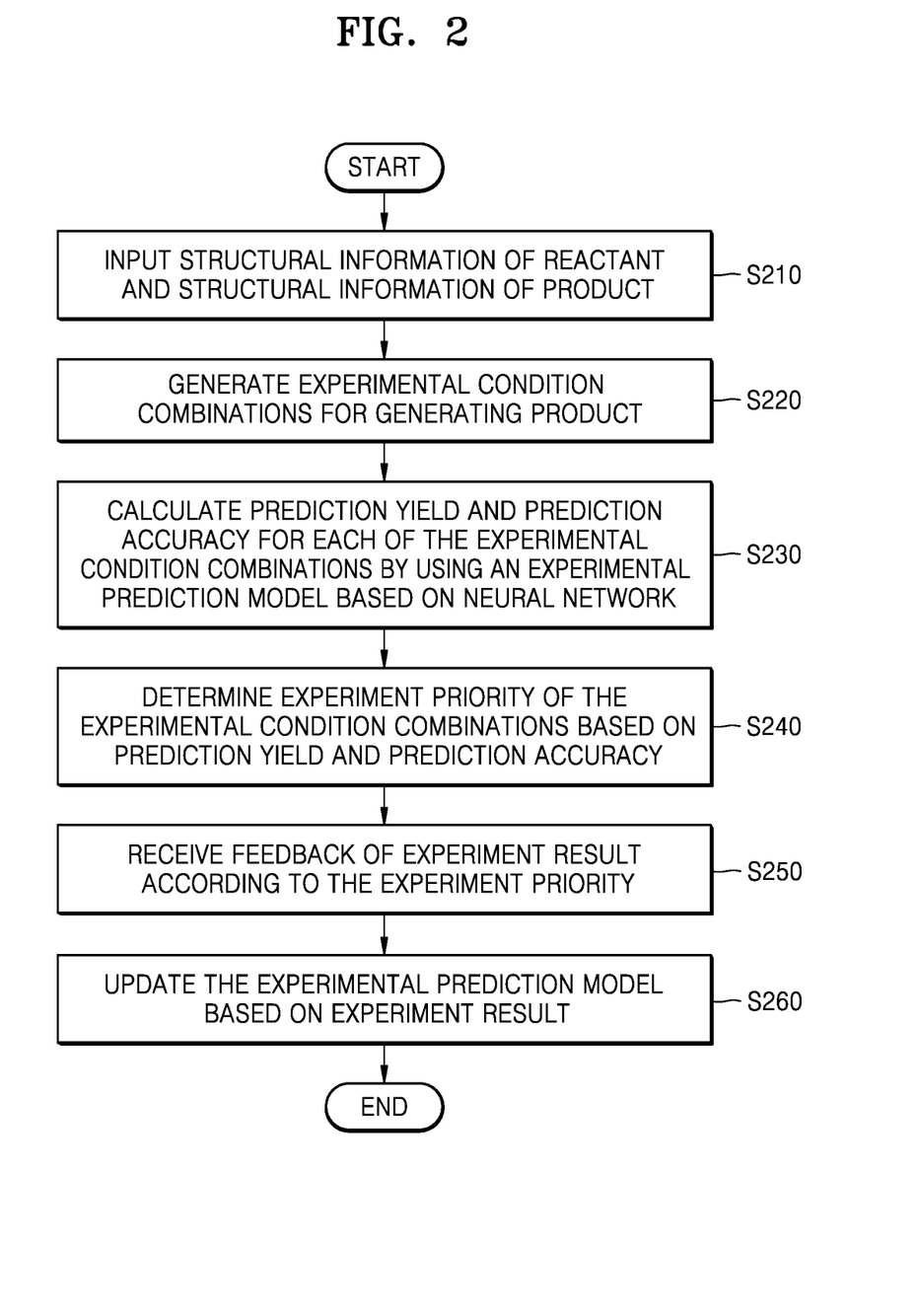
FIG. 2 is a flowchart illustrating a method of optimizing experimental conditions, according to an example embodiment.

FIG. 2 is a flowchart illustrating a method of optimizing experimental conditions, according to an example embodiment.

Referring to FIG. 2, a neural network apparatus may receive structural information of a reactant and structural information of a product (S210).

In one example embodiment, the neural network apparatus may receive the structural information of the reactant and the structural information of the product through a user interface.

The neural network apparatus may receive the structural information of the reactant and the structural information of the product in the form of a descriptor. The descriptor is an index value used to express a feature of a substance, and a value that may be obtained by performing a relatively simple computational process on a given substance. For example, the neural network apparatus may receive structural information of a reactant and structural information of a product in the form of an extended connectivity fingerprint (ECFP).

According to an example embodiment, the neural network apparatus may also receive a reaction method of producing a product through the reactant. The neural network apparatus may receive the reaction method in the form of a one-hot vector. For example, when the neural network apparatus receives a second method of four reaction methods, the one-hot vector that is input to the neural network apparatus may be represented by 0100.

The neural network apparatus may generate experimental condition combinations by combining experimental conditions for producing a product (S220).

The experimental conditions may include factors that affect a reaction rate, product yield, etc. and may denote conditions such as, for example but not limited thereto, a catalyst condition, a base condition, a solvent condition, a reagent condition, a temperature condition, and a reaction time condition.

The experimental condition combination is for obtaining an optimal yield and may denote a combination of experimental conditions including at least one experimental condition.

In one example embodiment, the neural network apparatus may generate experimental condition combinations based on the structural information of the reactant and the structural information of the product.

In another example embodiment, the neural network apparatus may generate experimental condition combinations based on the reaction method when the reaction method is input together with the structural information of the reactant and the structural information of the product. For example, when the input reaction method is a Suzuki-miyaura method, a chemical species of a nucleophile, such as palladium may be selected as a catalyst condition and 15 minutes may be selected as a reaction time condition.

The processor 110 may generate and provide a plurality of experimental condition combinations.

In one example embodiment, the neural network apparatus may set a plurality of experimental condition combinations, and the same kind of an experimental condition may be included in each of the plurality of experimental condition combinations. For example, the neural network apparatus may be set to include a catalyst A and a reaction time of 10 minutes in the first experimental condition combination, and be set to include a catalyst B and a reaction time of 20 minutes in the first experimental condition combination. In other words, the neural network apparatus may set a plurality of experimental condition combinations so that the catalyst condition and the reaction time condition are equally included in the first experimental condition combination and the second experimental condition combination.

In another example embodiment, the neural network apparatus may set a plurality of experimental condition combinations, and at least one of the types of experimental conditions included in each of the plurality of experimental condition combinations may be different. For example, the neural network apparatus may be set to include a catalyst C and a reaction time of 30 minutes in the first experimental condition combination, and be set to include a base D and a temperature E ° C. in the second experimental condition combination. In other words, the neural network apparatus may set a catalyst condition and a reaction time condition to be included in the first experimental condition combination, and may set a base and a temperature condition, different from the type of the experimental condition included in the first experimental condition combination, to be included in the second experimental condition combination.

The neural network apparatus may generate an experimental condition group including a plurality of experimental condition combinations. The experimental condition group may denote a set of experimental condition combinations to determine an experiment priority. The neural network apparatus may determine the experiment priority among the combinations of experimental conditions included in the experimental condition group.

The neural network apparatus may calculate a prediction yield and a prediction accuracy of a product for each combination of experimental conditions by using the neural network-based experimental prediction model (S230).

The neural network-based experimental prediction model may be a model generated by the processor 110 through machine learning based on a database, such as Reaxys or SciFinder.

In one example embodiment, the processor 110 may generate experimental condition combinations through machine learning by using the structural feature of a reactant and the structural feature of a product and may calculate a prediction yield and a prediction accuracy of the product for each of the experimental condition combinations.

In another example embodiment, the processor 110 may generate experimental condition combinations through machine learning by using a structural feature of a reactant, a structural feature of a product, and a reaction method and may calculate a predicted yield and a prediction accuracy of the product for each of the experimental condition combinations.

The neural network apparatus may determine the experiment priority among the combination of experimental conditions based on the prediction yield and the prediction accuracy (S240).

As an example, when prediction accuracies of the experimental condition combinations are higher than a predetermined reference accuracy, the processor 110 may determine the experiment priority among the experiment condition combinations in the order of high prediction yield. As another example, when the prediction yields of the experimental condition combinations are all less than the predetermined reference yield, the processor 110 may determine the experiment priority of the experimental condition combinations in the order of low prediction accuracy.

The neural network apparatus may provide experimental condition combinations according to the experiment priority for the progress of the experiment.

In one example embodiment, the neural network apparatus may output a priority of the experimental condition combinations through a predetermined display method (not shown) so that a user performs an actual experiment according to the priority. In another example embodiment, the neural network apparatus may convert the priority experimental condition combinations into a predetermined signal and output the converted signal so that an experimental device (not shown) connected to the neural network apparatus performs an actual experiment according to the priority.

The neural network apparatus may receive feedback of the experiment result according to the experiment priority (S250).

The neural network apparatus may receive an experiment result corresponding to the experimental condition combinations. The experiment may be performed by a user or automatically by an experimental device (not shown) connected to a neural network apparatus.

The neural network apparatus may update the experimental prediction model based on the experiment result (S260).

The neural network apparatus may update the experimental prediction model based on the feedback of the experiment results. For example, the neural network apparatus may update the experimental prediction model by using Bayesian optimization, but is not limited thereto.

Figure 3:
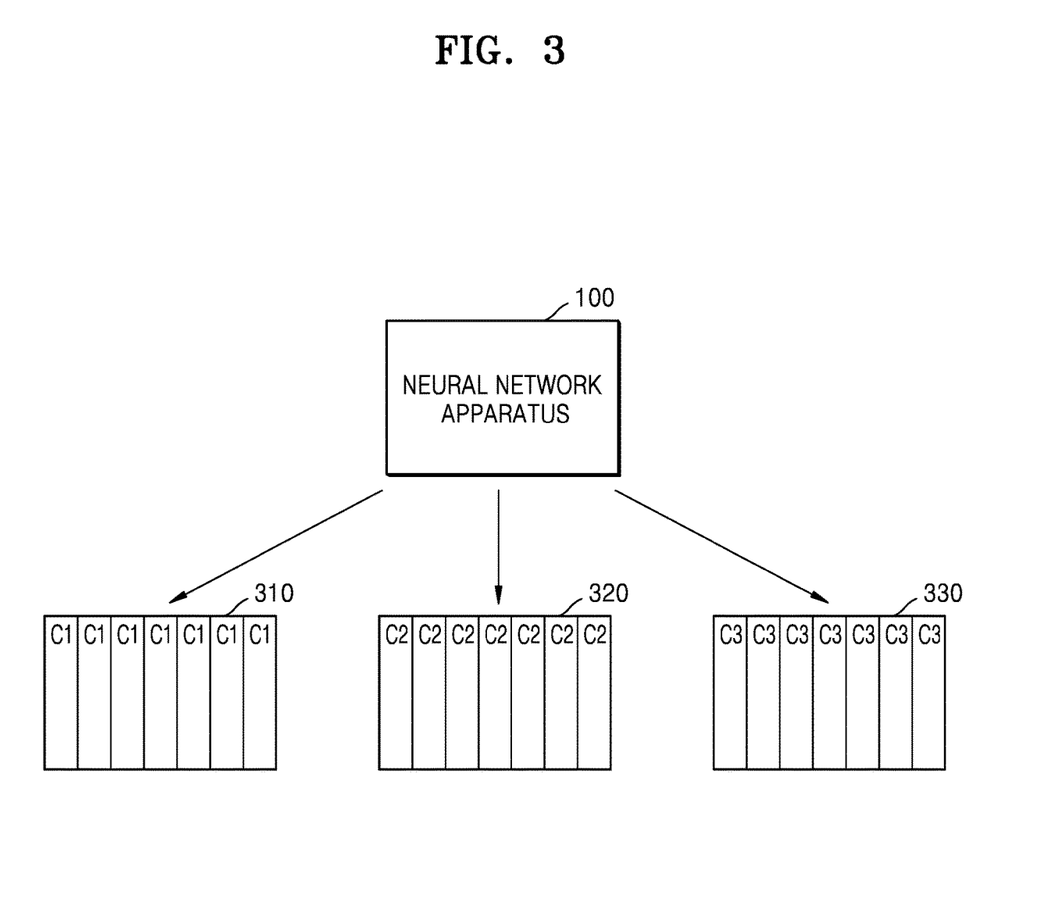
FIG. 3 is a diagram for explaining an example of experimental condition combinations according to an example embodiment.

FIG. 3 is a diagram for explaining an example of experimental condition combinations according to an example embodiment.

Referring to FIG. 3, the neural network apparatus 100 may generate a plurality of experimental condition groups so that each of the plurality of experimental condition combinations is included in any one of the plurality of experimental condition groups. For example, the neural network apparatus 100 may generate a first experimental condition group 310, a second experimental condition group 320, and a third experimental condition group 330.

When the neural network apparatus 100 generates a plurality of groups, it is possible to perform experiments in parallel. In FIG. 3, three experimental condition groups, that is, the first to third experimental condition groups 310, 320, and 330, are illustrated, and each of the first to third experimental condition groups 310, 320, and 330 is illustrated as including seven experimental condition combinations, but is not limited thereto.

When the neural network apparatus 100 generates a plurality of experimental condition groups, the neural network apparatus 100 may be set such that a specific experimental condition that most affects the prediction yield is not to be overlapped each other in the plurality of experimental condition groups. For example, if the specific experimental condition that most affects the predicted yield is a catalytic condition, the processor 110 may dispose a first catalyst C1 in the first experimental condition group 310, a second catalyst C2 in the second experimental condition group 320, and a third catalyst C3 in the third experimental condition group 330.

Since a specific experimental condition that most affects the predicted yield is separately disposed in a plurality of groups of experimental conditions, it is possible to quickly determine whether a measured yield reaches a target yield. In this case, the measured yield may denote an actual yield obtained when an actual experiment is performed by using a predetermined experimental condition.

Figure 4A:
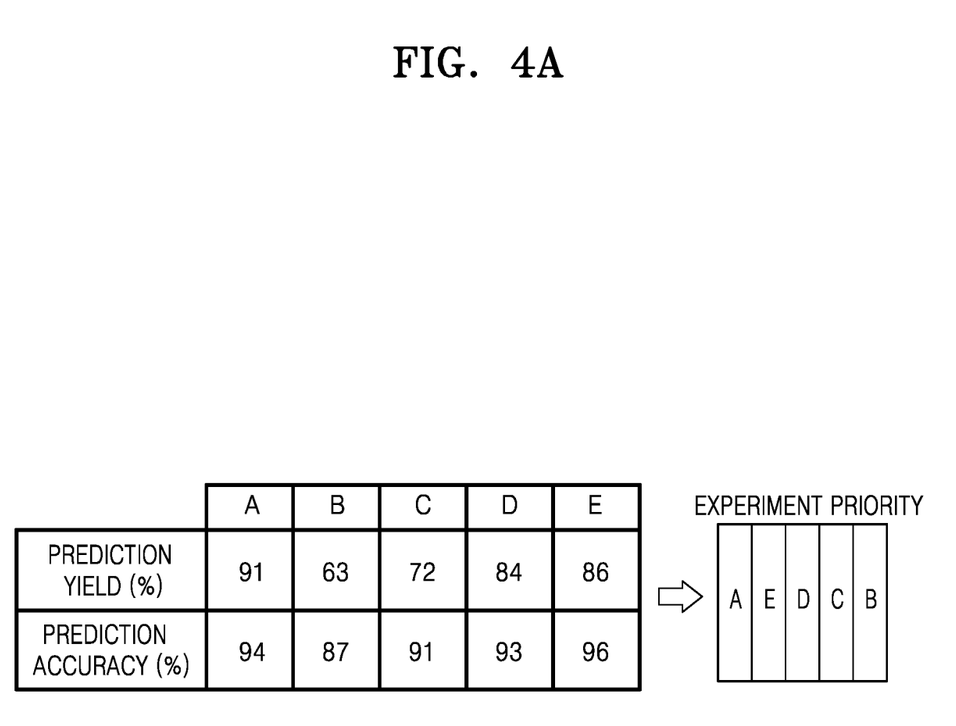
FIGS. 4A and 4B are diagrams for explaining a prediction yield and prediction accuracy by using an experimental prediction model based on a neural network and a method of determining priority using the prediction yield and prediction accuracy, according to an example embodiment.
Figure 4B:
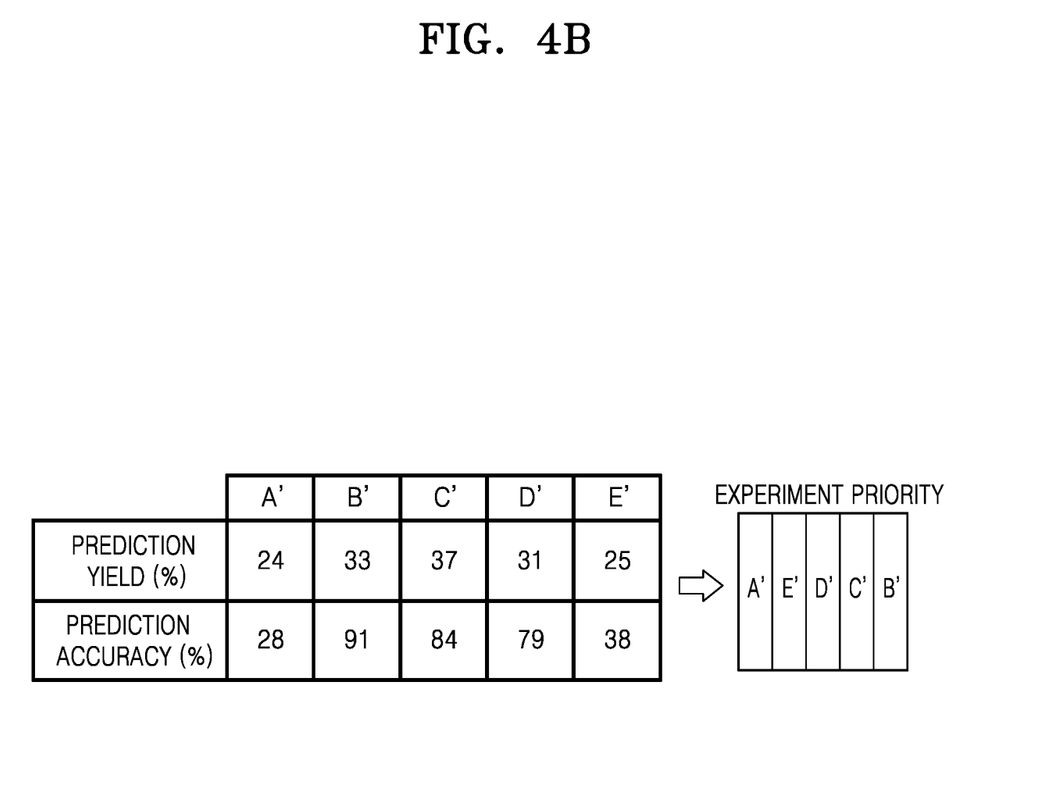

FIGS. 4A and 4B are diagrams for explaining a prediction yield and a prediction accuracy by using an experimental prediction model based on a neural network and a method of determining a priority using the prediction yield and the prediction accuracy, according to an example embodiment.

Tables in FIGS. 4A and 4B show calculation results of prediction yields and prediction accuracies of products for each combination of experimental conditions by using a neural network-based experimental prediction model. Reference characters A, B, C, D, and E and A', B', C', D' and E' respectively may refer to an experimental condition combination. Each experimental condition combination may include at least one experimental condition.

In FIG. 4A, the neural network apparatus may select experimental condition combinations having a prediction accuracy greater than a predetermined reference accuracy. For example, the reference accuracy may be 80%. In FIG. 4A, since all experimental condition combinations included in the experimental condition group have a prediction accuracy above the reference accuracy, the neural network apparatus may select all of the A to E experimental condition combinations.

The neural network apparatus may determine the experiment priority of the experimental condition combinations in the order of a high prediction yield. In FIG. 4A, since the prediction yield is high in the order of A->E->D->C->B (a descending order), the neural network apparatus may determine the experiment priority in the order of A->E->D->C->B. As the neural network apparatus selects the experimental condition combinations of which prediction accuracy is above the reference accuracy, determines the experiment priority among the experimental condition combinations based on the predicted yield, and performs an experiment by using the experimental condition combinations according to the experiment priority, it is possible to further quickly obtain a measured yield expected by the user (or a target yield).

In FIG. 4B, when a predicted yield of all of the experimental condition combinations is less than a predetermined reference yield, the neural network apparatus may determine the experiment priority of the experimental condition combinations in the order of low prediction accuracy. The reference yield may be set significantly lower than a target yield described below. For example, the reference yield may be 40%. In FIG. 4B, since all experimental condition combinations have a predicted yield less than the reference yield, the neural network apparatus may determine the experiment priority in the order of low prediction accuracy, that is, A'->E'->D'->C'->B' in the example of FIG. 4B.

Figure 5:
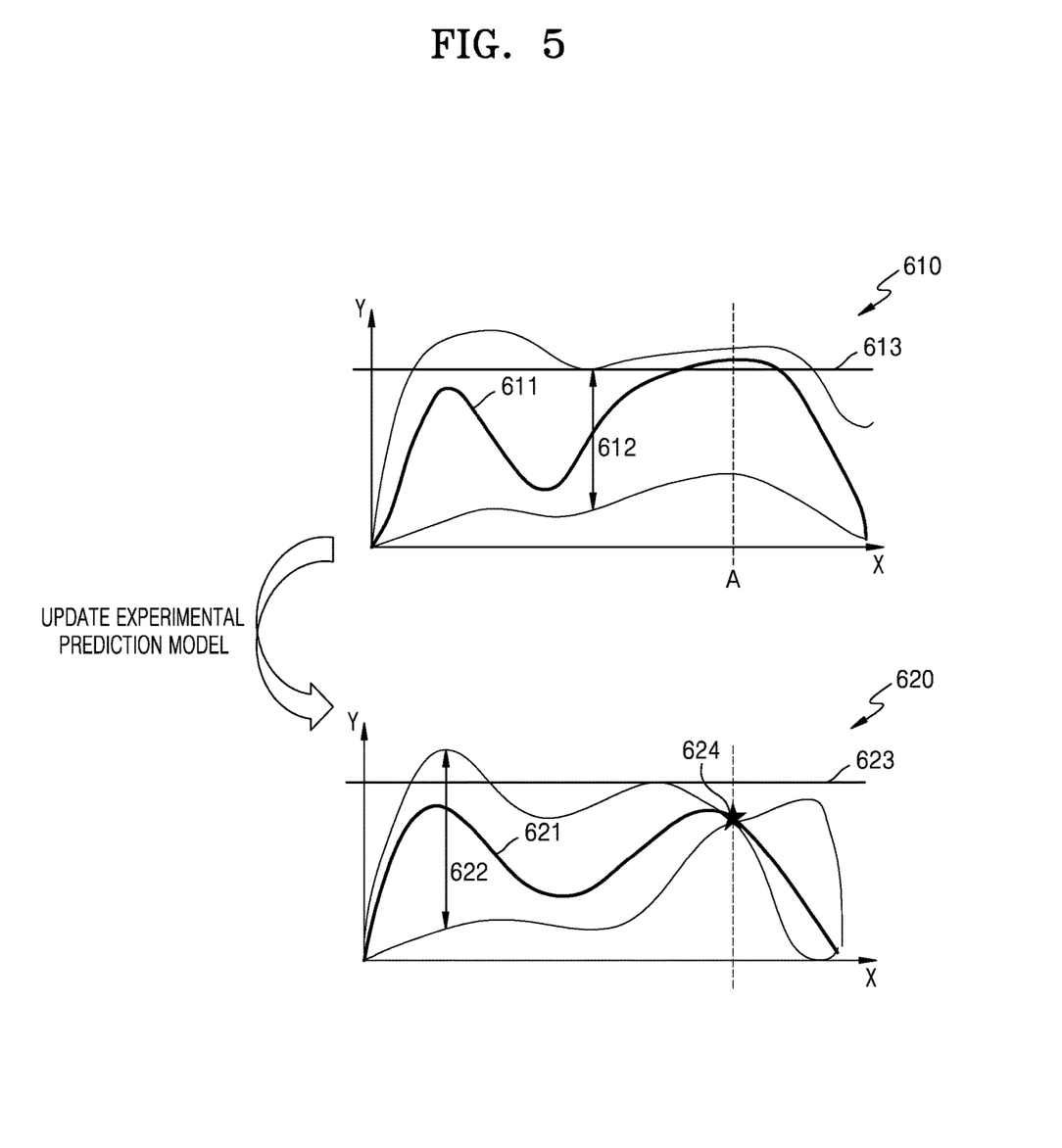
FIG. 5 is a graph for explaining a process of updating an experimental prediction model according to an example embodiment.

FIG. 5 is a graph for explaining a process of updating an experimental prediction model according to an example embodiment.

FIG. 5 is a graph showing a yield (y-axis) according to an experimental condition combination (x-axis). In detail, FIG. 5 shows a first graph 610 before updating an experimental prediction model and a second graph 620 after updating an experimental prediction model, and prediction yields 611 and 621, prediction accuracies 612 and 622, and target yields 613 and 623 of a prediction model are respectively shown in the first and second graphs 610 and 620. The prediction accuracies 612 and 622 of the prediction model denote neural network-based prediction accuracies, such as prediction accuracies based on DNN, RNN, CVAE, etc., and the narrower an interval denoted by 612 or 622 between upper and lower graphs, it indicates that the higher the accuracy of prediction is.

The neural network apparatus may provide an experimental condition combination having high a prediction yield 611 and a high prediction accuracy 612 as an experimental condition to be tested at a higher priority. For example, since the prediction yield 611 and the prediction accuracy 612 of the experimental condition combination A are high in the first graph 610 of FIG. 5, the neural network apparatus may provide the experimental condition combination A to a user or an experimental device as an experimental condition to be tested at a higher priority.

In one example embodiment, the neural network apparatus may output a priority of an experiment condition combination through a predetermined display method so that a user performs an actual experiment according to the priority. In another example embodiment, the neural network apparatus may convert the priority of experimental condition combinations into a predetermined signal and output the predetermined signal so that an experimental device connected to the neural network apparatus performs an actual experiment according to the priority.

The neural network apparatus may receive an experiment result according to the priority of an experimental condition combination. For example, in the second graph 620 of FIG. 5, the neural network apparatus may receive an experiment result 624 according to the experimental condition combination A.

The neural network apparatus may update an experimental prediction model based on the experiment results according to the priority of an experimental condition combination. In this case, the neural network apparatus may perform a Bayesian optimization process based on the experiment result according to the priority of an experimental condition combination. In one example embodiment, the neural network apparatus may optimize an experimental prediction model by using Gaussian Processes (GP) of a surrogate model based on an experiment result. Also, the neural network apparatus may perform probabilistic estimation with respect to a prediction yield by using a mean function and a covariance function of the prediction yield based on the experiment result.

For example, in FIG. 5, the neural network apparatus may perform a Bayesian optimization process of the experimental prediction model based on the experimental condition combination A. According to the Bayesian optimization of the experimental prediction model, the first graph 610 may be optimized as the second graph 620. In other words, the prediction accuracy 622 of the second graph 620 may be generally increased than the prediction accuracy 612 of the first graph 610. As the experimental prediction model is updated, the prediction yield 611 of the first graph 610 may be changed to be the prediction yield 621 of the second graph 620, and as a result, the experiment priority of experimental condition combinations of low priority in the first graph 610 before updating may be changed to have higher priority in the second graph 620 after the updating.

The neural network apparatus may re-determine the experiment priority of experimental condition combinations of low priority based on the updated experimental prediction model and may repeat an updating process of the experimental prediction model based on the re-determined experiment priority. Methods of re-determining the experiment priority of the experimental condition combinations and updating of the experimental prediction model accordingly will be described below with reference to FIGS. 6 and 7. As the number of feedbacks of the experiment results increases, the degree of optimization of the experimental prediction model may be increased.

Figure 6:
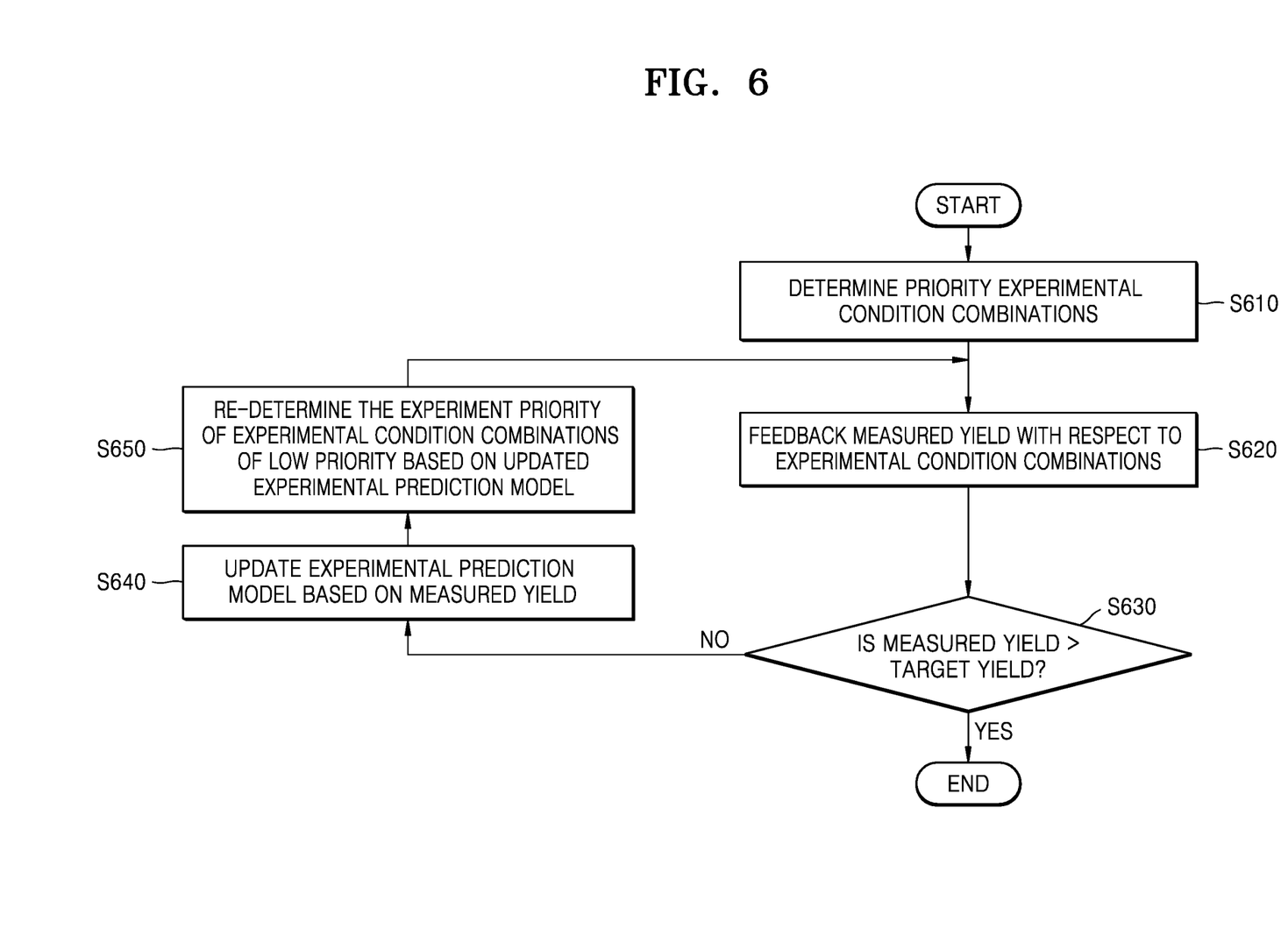
FIG. 6 is a flowchart illustrating a method of updating an experimental prediction model, according to an example embodiment.

FIG. 6 is a flowchart illustrating a method of updating an experimental prediction model, according to an example embodiment.

Referring to FIG. 6, a neural network apparatus may determine priority experimental condition combinations (S610). The priority experimental condition combinations may denote experimental condition combinations having the highest priority among experimental condition combinations to be tested. The neural network apparatus may determine experimental condition combinations having the highest prediction accuracy as the priority experimental condition combinations among the experimental condition combinations having a prediction accuracy higher than a preset reference accuracy.

The neural network apparatus may receive feedback of a measured yield with respect to the experimental condition combinations determined as priority (S620). The measured yield may denote a yield of a product through an actual experiment, and may be fed back by an input by a user or by an experimental device connected to the neural network apparatus.

The neural network apparatus may compare a measured yield with a target yield (S630). The target yield may denote a desired yield by the user, and in one example embodiment, the target yield may be input through a user interface. For example, the target yield may be 90%. The neural network apparatus may terminate the update of the experimental prediction model when the measured yield is greater than the target yield. According to an example embodiment, the neural network apparatus may terminate the update of the experimental prediction model after reflecting the measured yield to the experimental prediction model.

If the measured yield is less than the target yield, the neural network apparatus may update the experimental prediction model based on the measured yield (S640). The neural network apparatus may update the experimental prediction model by using Bayesian optimization.

The neural network apparatus may re-determine the experiment priority of experimental condition combinations of low priority based on the updated experimental prediction model (S650). In other words, as the experimental prediction model is updated, the experiment priority of experimental condition combinations of low priority may be changed.

Since the neural network apparatus receives feedback of the experiment result and changes the experiment priority for experiment condition combinations of low priority in real time by reflecting the feedback result, a predicted yield expected by the user (or a target yield) may be further quickly obtained.

The neural network apparatus may repeat the update of the experimental prediction model until the measured yield fed back reaches the target yield.

Figure 7:
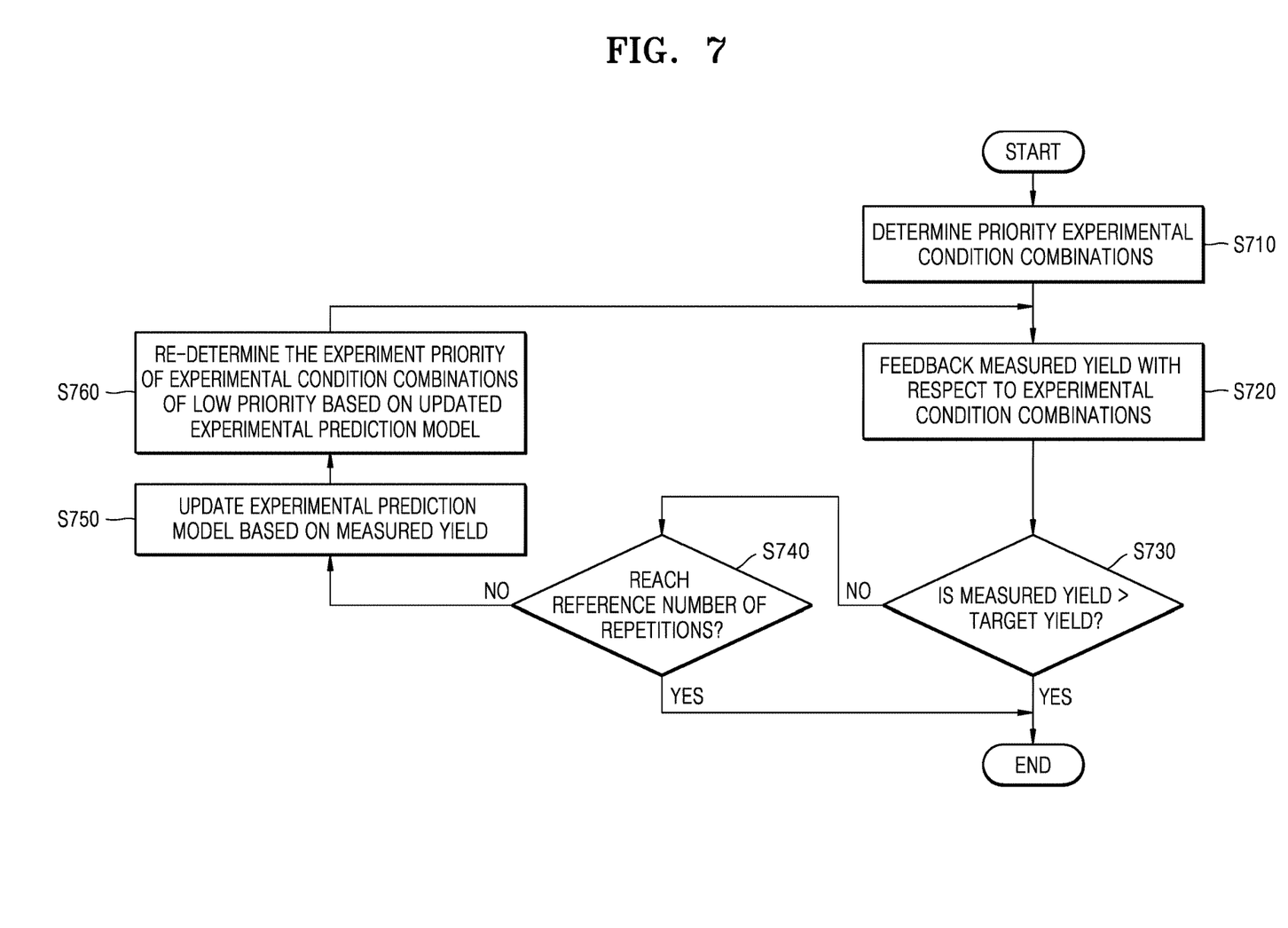
FIG. 7 is a flowchart for explaining a method of updating an experimental prediction model, according to another example embodiment.

FIG. 7 is a flowchart for explaining a method of updating an experimental prediction model, according to another example embodiment. A difference from FIG. 6 is the number of update repetitions of the experimental prediction model.

Referring to FIG. 7, a neural network apparatus may determine priority experimental condition combinations (S710). The neural network apparatus may determine experimental condition combinations having the highest prediction accuracy as the priority experimental condition combinations among the experimental condition combinations having a prediction accuracy higher than a preset reference accuracy.

The neural network apparatus may receive feedback of a measured yield with respect to the experimental condition combinations determined as priority (S720).

The neural network apparatus may compare a measured yield with a target yield (S730). The neural network apparatus may terminate the update of the experimental prediction model when the measured yield is greater than the target yield. According to an example embodiment, the processor 110 may terminate the update of the experimental prediction model after reflecting the measured yield to the experimental prediction model.

The neural network apparatus may calculate whether the number of update repetitions reaches a preset reference repetitions (S740). The number of update repetitions may be appropriately set in consideration of time, cost, etc. required for the experiment.

If the number of update repetitions does not reach the number of preset reference repetitions, the neural network apparatus may update the experimental prediction model based on the measured yield (S750) and may re-determine the experiment priority of experimental condition combinations of low priority based on the updated experimental prediction model (S760).

When the number of update repetitions reaches the preset reference repetitions, the neural network apparatus may terminate updating of the experimental prediction model. If the experiment was performed in the number of preset reference repetitions but a target yield of a product could not be reached, it is advantageous to early terminate the experiment or to perform a bypass experiment instead of continuing to perform the experiment.

Example embodiments of the inventive concept may be implemented as a non-transitory computer-readable program, and may be realized in general computers that execute the program by using a non-transitory computer-readable recording medium. In addition, the structure of the data used in the above example embodiments may be recorded on the non-transitory computer-readable recording medium through various means. The computer-readable medium may include magnetic storage media (e.g., ROM, floppy disks, hard disks, etc.), optical recording media (e.g., CD-ROMs or DVDs), and transmission media, such as Internet transmission media.

It will be understood by those of ordinary skill in the art that various changes in form and details may be made therein without departing from the spirit and scope of the inventive concept. Therefore, the example embodiments should be considered in descriptive sense only and not for purposes of limitation. The scope of the inventive concept is defined not by the detailed description of the inventive concept but by the appended claims, and all differences within the scope will be construed as being included in the inventive concept.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method of optimizing experimental conditions by using a neural network, the method comprising:
   receiving, in a form of a descriptor, structural information of a reactant and structural information of a product, the structural information indicating a structure of an atom level of a substance included in the reactant or the product, wherein the descriptor is an index value used to express a feature of the substance;
   generating, based on the structural information of the reactant and the structural information of the product, experimental condition combinations by combining one or more experimental conditions for producing the product;
   calculating a prediction yield of the product and a prediction accuracy of the prediction yield for each of the experimental condition combinations by using an experimental prediction model based on a neural network;
   determining an experiment priority of a respective experimental condition combination based on the prediction yield and the prediction accuracy, wherein when all of prediction yields of the experimental condition combinations are less than a first predetermined reference yield, the experiment priority is determined in an order of a low prediction accuracy such that an experimental condition combination having a lowest prediction accuracy has a highest experiment priority; and
   updating the experimental prediction model based on a result of an experiment, which is preferentially performed according to a higher experiment priority.

2. The method of claim 1, wherein when not all of the prediction yields of the experimental condition combinations are less than the first predetermined reference yield, and at least one experimental condition combination has a prediction accuracy greater than a predetermined reference accuracy, the determining comprises: determining an experiment priority of the at least one experimental condition combination in an order of a high prediction yield.

3. The method of claim 1, wherein the updating comprises:
   updating the experimental prediction model based on a measured yield of the product obtained with respect to an experimental condition combination having a high priority, in response to the measured yield being less than a predetermined target yield; and
   re-determining the experiment priority of an experimental condition combination having a low priority based on the updated experimental prediction model.

4. The method of claim 3, wherein the updating the experimental prediction model is repeated until the measured yield reaches a target yield.

5. The method of claim 3, wherein the updating the experimental prediction model is terminated when a number of a repetition of the updating reaches a preset reference number.

6. The method of claim 1, wherein the determining comprises:
   generating experimental condition groups, each of the experimental condition combinations being included in any one of the experimental condition groups; and
   determining an experiment priority of a respective experimental condition combination included in each of the experimental condition groups.

7. The method of claim 6, wherein the generating the experimental condition groups comprises generating the experimental condition groups in a manner such that an experimental condition that most affects the prediction yield is not to be overlapped each other in the experimental condition groups.

8. The method of claim 1, wherein the receiving comprises receiving the structural information of the reactant and the structural information of the product in a form of an extended connectivity fingerprint (ECFP).

9. The method of claim 1, wherein the one or more experimental conditions comprise at least one of a catalyst condition, a base condition, a solvent condition, a reagent condition, a temperature condition, and a reaction time condition.

10. A neural network apparatus for optimizing experimental conditions, the neural network apparatus comprising:
  a user interface configured to receive, in a form of a descriptor, structural information of a reactant and structural information of a product, the structural information indicating a structure of an atom level of a substance included in the reactant or the product, wherein the descriptor is an index value used to express a feature of the substance;
  a memory configured to store at least one program; and
  a processor configured to operate a neural network by executing the at least one program, wherein
  the processor is further configured to:
    generate, based on the structural information of the reactant and the structural information of the product, experimental condition combinations by combining one or more experimental conditions for producing the product;
    calculate a prediction yield of the product and a prediction accuracy of the prediction yield with respect to each of the experimental condition combinations by using an experimental prediction model based on a neural network;
    determine an experiment priority of a respective experimental condition combination based on the prediction yield and the prediction accuracy, wherein when all of prediction yields of the experimental condition combinations are less than a first predetermined reference yield, the experiment priority is determined in an order of a low prediction accuracy such that an experimental condition combination having a lowest prediction accuracy has a highest experiment priority; and
    update the experimental prediction model based on a result of an experiment, which is preferentially performed according to a higher experiment priority.

11. The neural network apparatus of claim 10, wherein when not all of the prediction yields of the experimental condition combinations are less than the first predetermined reference yield, and at least one experimental condition combination has a prediction accuracy greater than a predetermined reference accuracy, the processor is further configured to: determine an experiment priority of the at least one experimental condition combination in an order of a high prediction yield.

12. The neural network apparatus of claim 10, wherein the processor is further configured to:
  update the experimental prediction model based on a measured yield of the product with respect to an experimental condition combination having a high priority, in response to the measured yield being less than a predetermined target yield, and
  re-determine the experiment priority of an experimental condition combination having a low priority based on the updated experimental prediction model.

13. The neural network apparatus of claim 12, wherein the processor is further configured to repeat updating the experimental prediction model in response to the measured yield being less than the predetermined target yield.

14. The neural network apparatus of claim 13, wherein the processor is further configured to terminate the updating the experimental prediction model when a number of a repetition of the updating reaches a preset reference number.

15. The neural network apparatus of claim 10, wherein the processor is further configured to:
  generate experimental condition groups, each of the experimental condition combinations being included in any one of the experimental condition groups, and
  determine an experiment priority of a respective experimental condition combination included in each of the experimental condition groups.

16. The neural network apparatus of claim 15, wherein the processor is further configured to generate the experimental condition groups in a manner such that an experimental condition that most affects the prediction yield is not to be overlapped each other in the experimental condition groups.

17. A non-transitory computer-readable recording medium having a program recorded thereon, the program, when executed by a computer, causes the computer to execute the method of claim 1.

* * * * *